US012590256B2

(12) United States Patent
Ul-haq et al.

(10) Patent No.: US 12,590,256 B2
(45) Date of Patent: Mar. 31, 2026

(54) CORROSION INHIBITOR FORMULATIONS BASED ON COMPOUNDS WITH BOTH PYRIDINIUM AND HYDROXY SUBSTITUENTS

(71) Applicant: Saudi Arabian Oil Company, Dhahran (SA)

(72) Inventors: Muhammad Imran Ul-haq, Dhahran (SA); Nayef M. Alanazi, Dhahran (SA); Turki M. Al Abeedi, Dhahran (SA); Abdullah Al-Malki, Dammam (SA); Faisal M. Al-Mutahhar, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 114 days.

(21) Appl. No.: 18/318,960

(22) Filed: May 17, 2023

(65) Prior Publication Data

US 2023/0383201 A1 Nov. 30, 2023

Related U.S. Application Data

(63) Continuation of application No. 17/728,181, filed on Apr. 25, 2022, now abandoned.

(51) Int. Cl.

*C07D 213/04* (2006.01)
*C09K 15/30* (2006.01)
*C10G 75/02* (2006.01)
*C23F 11/14* (2006.01)

(52) U.S. Cl.

CPC ........... *C10G 75/02* (2013.01); *C07D 213/04* (2013.01); *C09K 15/30* (2013.01); *C23F 11/149* (2013.01); *C10G 2300/4075* (2013.01)

(58) Field of Classification Search

CPC .................................................... C07D 213/04
See application file for complete search history.

(56) References Cited

U.S. PATENT DOCUMENTS

| | | | |
|---|---|---|---|
| 3,109,846 A * | 11/1963 | Klass et al. ............. C09B 57/00 8/919 | |
| 3,623,979 A | 11/1971 | Maddox et al. | |
| 3,629,104 A | 12/1971 | Maddox et al. | |
| 3,945,824 A | 3/1976 | Sakai et al. | |
| 4,515,708 A | 5/1985 | Haslegrave et al. | |
| 4,637,899 A | 1/1987 | Kennedy, Jr. | |
| 4,672,118 A | 6/1987 | Fisk et al. | |
| 4,673,436 A | 6/1987 | Haslegrave et al. | |
| 4,744,948 A | 5/1988 | Incorvia | |
| 4,784,796 A | 11/1988 | Treybig et al. | |
| 4,812,263 A | 3/1989 | Login | |
| 5,000,873 A | 3/1991 | Fisk et al. | |
| 5,292,480 A | 3/1994 | Fischer et al. | |
| 5,336,441 A | 8/1994 | Shah et al. | |
| 5,611,991 A | 3/1997 | Naraghi | |
| 5,993,693 A | 11/1999 | Meyer | |
| 6,118,000 A | 9/2000 | Frenier | |
| 6,303,079 B1 | 10/2001 | Meyer | |
| 7,057,050 B2 | 6/2006 | Meyer | |
| 7,951,754 B2 | 5/2011 | Tiwari et al. | |
| 9,074,289 B2 | 7/2015 | Malwitz et al. | |
| 9,238,588 B2 | 1/2016 | Harrington et al. | |
| 9,382,467 B2 | 7/2016 | Meyer et al. | |
| 9,434,911 B2 | 9/2016 | Bennett et al. | |
| 9,816,024 B2 | 11/2017 | Jafar Mazumder et al. | |
| 9,868,894 B1 | 1/2018 | Jafar Mazumder et al. | |
| 10,221,368 B2 | 3/2019 | Benitez Aguilar et al. | |
| 10,323,327 B2 | 6/2019 | Obot et al. | |
| 10,604,710 B2 | 3/2020 | Moloney | |
| 2008/0308770 A1 | 12/2008 | Tiwari | |
| 2010/0219379 A1 | 9/2010 | Acosta et al. | |
| 2013/0233543 A1 | 9/2013 | Overkempe et al. | |
| 2018/0282606 A1 | 10/2018 | Rodgers et al. | |
| 2020/0318243 A1 | 10/2020 | Obot et al. | |

FOREIGN PATENT DOCUMENTS

| | | | |
|---|---|---|---|
| CA | 2196650 | A1 | 8/1998 |
| CN | 103922997 | B | 2/2016 |
| CN | 111362867 | A | 7/2020 |
| EP | 1690960 | A2 | 8/2006 |
| JP | 2000038690 | A | 2/2000 |
| JP | 2000096049 | A | 4/2000 |
| JP | 3207183 | B2 | 9/2001 |
| WO | 9933953 | A1 | 7/1999 |

OTHER PUBLICATIONS

Madaan et al, Journal of Oleo Science, vol. 57, No. 4, pp. 197-215 (Year: 2008).*

Shibata et al., "Reactions and Utilization of long-chain alkylene oxides, III, Reactions of 1,2-epoxydodecane with varios amino compounds", Kogyou Kagaku Zasshi, vol. 68, No. 5, 1965, 5 pages.

Cao et al., "Preparation method of electrochromic material, and application in mobile terminal and shell component", Chemical Abstracts 173:L 493381, CN 111362867 (English Translation), 2020.

Demberelnyamba et al., "New Epoxide Molten Salts: Key Intermediates for Designing Novel Ionic Liquids", Chemistry Letters, vol. 33, No. 5, 2004 (2 pages).

(Continued)

*Primary Examiner* — John S Kenyon

(74) *Attorney, Agent, or Firm* — DINSMORE & SHOHL LLP

(57) ABSTRACT

Compounds for inhibiting corrosion are provided that include a pyridinium substituent and a hydroxy substituent. Also provided are methods of making the compounds. Also provided are corrosion inhibitor formulations including the compounds. Also provided are processes for inhibiting corrosion of a metallic surface using the corrosion inhibitor formulations.

6 Claims, 1 Drawing Sheet

(56) References Cited

OTHER PUBLICATIONS

Notification of Transmittal of the International Search Report and the Written Opinion of the International Searching Authority, or the Declaration dated Jun. 14, 2023 pertaining to International application No. PCT/US2023/015773 filed Mar. 21, 2023, pp. 1-15.

* cited by examiner

CORROSION INHIBITOR FORMULATIONS BASED ON COMPOUNDS WITH BOTH PYRIDINIUM AND HYDROXY SUBSTITUENTS

CROSS-REFERENCE TO RELATED APPLICATION

This application is a continuation application of U.S. patent application Ser. No. 17/728,181 filed Apr. 25, 2022, entitled "Systems and Processes for Upgrading and Converting Crude Oil to Petrochemicals Through Steam Cracking", the entire disclosure of which is incorporated by reference in the present disclosure.

TECHNICAL FIELD

Embodiments of the present disclosure generally relate to compositions and methods for inhibiting corrosion and, more specifically, to corrosion inhibitor formulations based on compounds with both pyridinium and hydroxy substituents and their use for mitigating corrosion of a metallic surface.

BACKGROUND

Corrosion is the irreversible interfacial reaction of a material with its environment, which results in the consumption of the material. According to a recent report by the National Association of Corrosion Engineers (NACE), the annual worldwide cost of corrosion is over 2.5 trillion U.S. dollars. In the oil and gas industry, corrosion can inflict severe damage on the internal walls of production and transportation pipelines, which are mostly steel based materials. Specifically, corrosion can lead to pipeline leakages and, in some cases, bursting. Such damage can result in high maintenance costs, discontinuity of operations, and low capacity production.

Sources of corrosion of metal surfaces include dissolved gasses, such as carbon dioxide ($CO_2$), which causes "sweet corrosion," and hydrogen sulfide ($H_2S$), which causes "sour corrosion." Once dissolved in water, both $CO_2$ and $H_2S$ behave like weak acids and can provide oxidizing power, which promotes steel corrosion. The more dominant of either sweet or sour corrosion in oilfield pipelines depends on the relative abundance of each gas in the environment. To mitigate sweet and sour corrosion during oil and gas production, transportation, and processing, corrosion inhibitors are commonly injected into pipeline fluids.

Mitigating pipeline corrosion in wet sour environments is a particular challenge for the oil and gas industry. Some of the most common corrosion inhibitor formulations are film formers based on nitrogen-containing compounds. They retard metallic corrosion by adsorbing onto the metal surface to create inhibitor barriers between the metal surface and the corrosive environment. Notable classes of corrosion inhibitor formulations include nitrogen-based compounds such as imidazolines, amines, and quaternary ammonium salts. Commonly used corrosion inhibitor formulations to mitigate corrosion in a wet sour environment include alkyl pyridinium benzyl quaternary ammnonium salts (APBQA). APBQAs form a relatively weak film barrier between the fluid phase and the metal surface. Thus, a high dosage of APBQA based corrosion inhibitor formulations is needed to significantly mitigate corrosion in a wet sour environment.

There is a need for corrosion inhibitor formulations that form a strong film barrier between the fluid phase and the metal surface of pipelines at lower dosages.

SUMMARY

Embodiments of the corrosion inhibitor formulations described herein meet this need through the inclusion of compounds comprising both pyridinium and hydroxy substituents. Such formulations exhibit superior corrosion inhibition efficiency relative to conventional corrosion inhibitor formulations in a wet sour environment even when applied at lower dosages.

In one or more embodiments, a compound for inhibiting corrosion is provided. The compound comprises Formula (I):

(I)

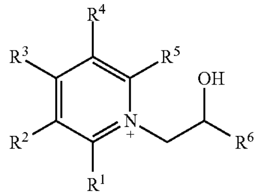

or a salt thereof. $R^1$, $R^2$, $R^3$, $R^4$, and $R^5$ are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide.

In some embodiments, a method of making the compound is provided. The method includes reacting a pyridine comprising Formula (II):

(II)

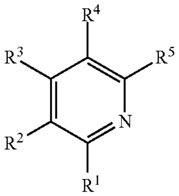

or a salt thereof, with an epoxide comprising Formula (III):

(III)

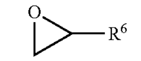

in the presence of an acid to produce the compound. $R^1$, $R^2$, $R^3$, $R^4$, and $R^5$ are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide.

In one or more embodiments, a sour well fluid including the compound at a concentration by weight of 0.1 parts per million to 100 parts per million of the well fluid is provided.

In some embodiments, a formulation for inhibiting corrosion is provided. The formulation includes the compound and water.

In one or more embodiments, a process for inhibiting corrosion is provided. The process includes contacting a metallic surface with the formulation.

In some embodiments, a process for inhibiting corrosion includes adding the formulation to a well fluid to effect a concentration by weight of the formulation in the well fluid of from 0.5 parts per million to 500 parts per million.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1A:
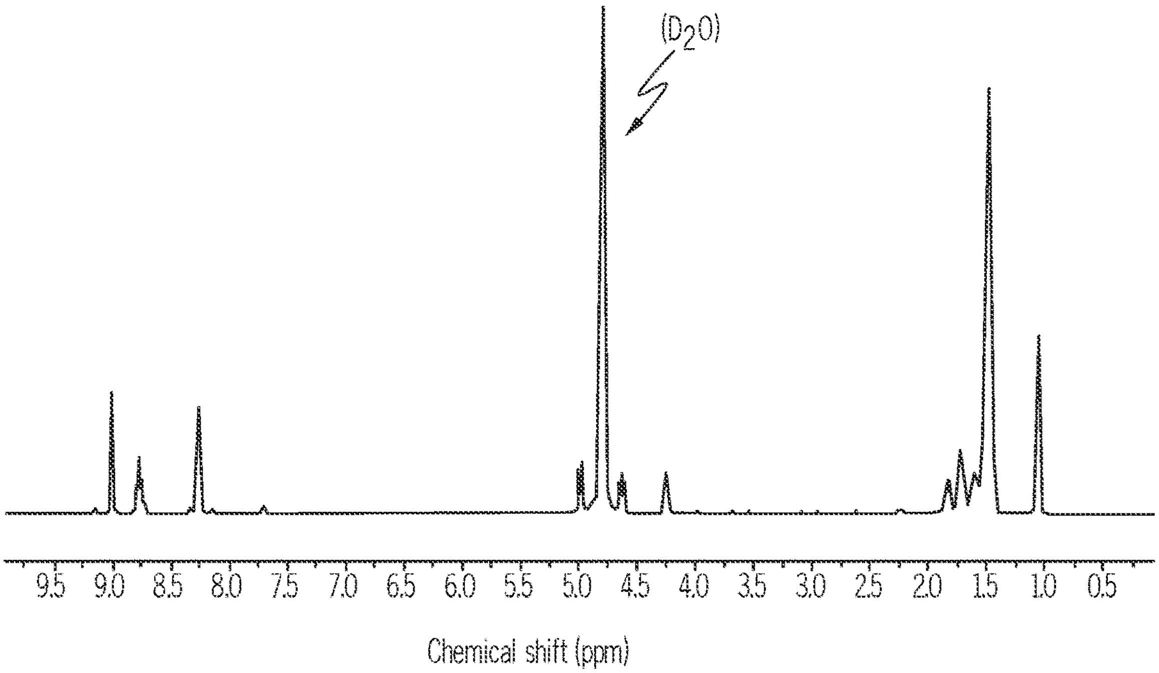
FIG. 1A is a $^1H$ nuclear magnetic resonance (NMR) spectrum of an embodiment of an active component according to embodiments described herein.

Reference will now be made in greater detail to various embodiments, some embodiments of which are illustrated in the accompanying drawings.

DETAILED DESCRIPTION

As used herein, the term "active component" is defined as a component in a corrosion inhibitor formulation that acts to mitigate corrosion of a material. Active components are distinguished from inactive components, which mainly serve as a vehicle to convey an active component. Corrosion inhibitor formulations according to embodiments described herein may include one or more active components.

As used herein, "the active component" refers to the component in a corrosion inhibitor formulation that acts to mitigate corrosion of a material to a greater extent than any other individual component in the corrosion inhibitor formulation.

It was discovered that embodiments of compounds described herein that include both a hydroxy substituent and a pyridinium substituent exhibit superior corrosion inhibiting efficiency compared with conventional corrosion inhibitors. Without being bound by theory, it is believed that compounds including both a pyridinium substituent and a hydroxy substituent are capable of forming a stronger film barrier between a fluid phase and a metal surface than conventional corrosion inhibitors. Specifically, it is believed that compounds according to embodiments described herein may form a particularly strong bond with a metal surface because the hydroxy substituent chemically adsorbs onto the metal and the pyridinium substituent adsorbs onto the metal through both chemical and physical interactions owing to its positive charge and $sp^2$ hybridization. Thus, it is believed that conventional corrosion inhibitors that do not include both a pyridinium substituent and a hydroxy substituent form a weaker bond with a metal surface than compounds according to embodiments described herein. As such, conventional corrosion inhibitors may be less effective at mitigating corrosion of metal surfaces than compounds according to embodiments described herein.

According to embodiments, a compound for inhibiting corrosion includes Formula (I):

(I)

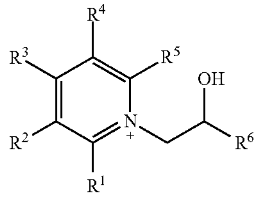

or a salt thereof. In some embodiments, $R^1$, $R^2$, $R^3$, $R^4$, and $R^5$ in Formula I are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. According to embodiments, $R^1$, $R^2$, $R^3$, $R^4$, and $R^5$ in Formula I are independently hydrogen, a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl. In some embodiments, $R^1$, $R^2$, $R^3$, $R^4$, and $R^5$ in Formula I are independently hydrogen.

According to one or more embodiments, $R^6$ in Formula I is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. In some embodiments, $R^6$ in Formula I is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl. According to embodiments, $R^6$ in Formula I is a substituted or unsubstituted $C_1$ to $C_{24}$ alkyl. In some embodiments, $R^6$ in Formula I is a substituted or unsubstituted $C_5$ to $C_{15}$ alkyl. Without being bound by theory, it is believed that the presence of a long alkyl chain may facilitate bonding with a metal surface. Further, it is believed that the presence of a long alkyl chain may provide superior protection against corrosion.

In some embodiments, a method of making the compound comprises reacting a pyridine comprising Formula (II):

(II)

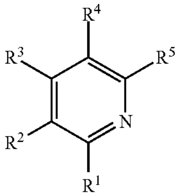

or a salt thereof, with an epoxide comprising Formula (III):

(III)

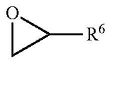

in the presence of an acid to produce the compound. In some embodiments, $R^1$, $R^2$, $R^3$, $R^4$, and $R^5$ in Formula II are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. According to embodiments, $R^1$, $R^2$, $R^3$, $R^4$, and $R^5$ in Formula II are independently hydrogen, a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl. In some embodiments, $R^1$, $R^2$, $R^3$, $R^4$, and $R^5$ in Formula II are independently hydrogen.

According to one or more embodiments, $R^6$ in Formula II is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. In some embodiments, $R^6$ in Formula II is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl. According to embodiments, $R^6$ in Formula II is a substituted or unsubstituted $C_1$ to $C_{24}$ alkyl. In some embodiments, $R^6$ in Formula II is a substituted or unsubstituted $C_5$ to $C_{15}$ alkyl.

In some embodiments, the acid comprises hydrochloric acid, sulfuric acid, phosphoric acid, hydrobromic acid, acetic acid, nitric acid, or a combination thereof. In embodiments, the acid comprises hydrochloric acid, phosphoric acid, sulfuric acid, or a combination thereof. According to one or more embodiments, the acid comprises hydrochloric acid.

In embodiments, the compound may be used to mitigate corrosion of a material. In some embodiments, the compounds may be used to mitigate corrosion of a metallic surface, such as a metallic surface in a wet sour environment. According to one or more embodiments, the compounds may be included in a sour well fluid to mitigate the corrosion of surfaces exposed to the sour well fluid. Thus, a sour well fluid may include the compound at a concentration by weight of 0.1 parts per million to 100 parts per million, 0.2 parts per million to 50 parts per million, 0.2 parts per million to 40 parts per million, 0.2 parts per million to 30 parts per million, 0.2 parts per million to 20 parts per million, 0.2 parts per million to 10 parts per million, 0.3 parts per million to 8 parts per million, 0.4 parts per million to 6 parts per million, 0.5 parts per million to 5 parts per million, 0.5 parts per million to 2 parts per million, or 1 part per million to 2 parts per million of the well fluid. In embodiments, the sour well fluid may further comprise petroleum hydrocarbons.

In embodiments, a process for mitigating corrosion of a metallic surface may include contacting the metallic surface with a solution comprising the compound at a concentration by weight of 0.1 parts per million to 100 parts per million, 0.2 parts per million to 50 parts per million, 0.2 parts per million to 40 parts per million, 0.2 parts per million to 30 parts per million, 0.2 parts per million to 20 parts per million, 0.2 parts per million to 10 parts per million, 0.3 parts per million to 8 parts per million, 0.4 parts per million to 6 parts per million, 0.5 parts per million to 5 parts per million, 0.5 parts per million to 2 parts per million, or 1 part per million to 2 parts per million of the well fluid. According to embodiments, the metallic surface comprises steel. In some embodiments, the metallic surface comprises carbon steel. In embodiments, the metallic surface may be contacted with the corrosion inhibitor at least one time, at least two times, at least three times, at least four times, or even at least five times. It should be understood that when the metallic surface is contacted with the corrosion inhibitor multiple times, each contacting may be accomplished using the same or different concentrations of the compound described herein.

In some embodiments, the compound described herein may be used as an active component in a formulation for inhibiting corrosion. According to one or more embodiments, a corrosion inhibitor formulation comprises the compound and water. In some embodiments, the corrosion inhibitor formulation further comprises a synergist, a surfactant, a supporting component, a secondary solvent, a coupling agent, an ethoxylated amine, or a combination thereof.

According to one or more embodiments, the compound is present in the corrosion inhibitor formulation at a concentration of from 0.1 to 50 weight percent, 0.2 to 40 weight percent, 0.3 to weight percent, 0.5 to 40 weight percent, 1 to 40 weight percent, 2 to 40 weight percent, 3 to weight percent, 4 to 40 weight percent, 5 to 40 weight percent, 5 to 35 weight percent, 5 to 30 weight percent, 5 to 25 weight percent, 5 to 20 weight percent, or 10 to 20 weight percent. In embodiments, water is present in the corrosion inhibitor formulation at a concentration of from to 99.9 weight percent, 20 to 99 weight percent, 20 to 95 weight percent, 20 to 90 weight percent, 30 to 90 weight percent, 40 to 90 weight percent, 50 to 90 weight percent, 50 to 80 weight percent, 60 to 80 weight percent, or 65 to 75 weight percent.

In some embodiments, the corrosion inhibitor formulation includes a synergist. The synergist may act to facilitate the adsorption of an active component comprising a quaternary ammonium or pyridinium substituent onto the surface of a metal. Without being bound by theory, it is believed that the synergist adsorbs onto a metal surface while also attracting an active component comprising a quaternary ammonium or pyridinium substituent. In some embodiments, the synergist comprises a thiol substituent. In other embodiments, the synergist is an alkyl iodide. According to one or more embodiments, the synergist is thioglycolic acid, 2-mercaptoethanol, or a combination thereof. In embodiments, the synergist is present in the corrosion inhibitor formulation at a concentration of from 0.1 to 20 weight percent, 0.2 to 20 weight percent, 0.3 to weight percent, 0.5 to 20 weight percent, 1 to 20 weight percent, 1 to 15 weight percent, 1 to weight percent, 2 to 10 weight percent, 2 to 8 weight percent, or 2 to 6 weight percent.

In embodiments, the corrosion inhibitor formulation includes a secondary solvent. The secondary solvent may act to clean the metal for adsorption of an active component. In embodiments, the secondary solvent comprises ethylene glycol, ethylene diamine, or combinations thereof. According to one or more embodiments, the secondary solvent is present in the corrosion inhibitor formulation at a concentration of from 0.1 to 20 weight percent, 0.2 to weight percent, 0.3 to 20 weight percent, 0.5 to 20 weight percent, 1 to 20 weight percent, 1 to 15 weight percent, 1 to 10 weight percent, 1 to 8 weight percent, 1 to 6 weight percent, or 2 to weight percent.

According to one or more embodiments, the corrosion inhibitor formulation includes a surfactant. In embodiments, the surfactant comprises an ethoxylated alcohol. According to one or more embodiments, the ethoxylated alcohol comprises a carbon chain length of $C_5$ to $C_{20}$, $C_8$ to $C_{18}$, $C_{10}$ to $C_{15}$, or $C_{12}$ to $C_{14}$. According to one or more embodiments, the surfactant is present in the corrosion inhibitor formulation at a concentration of from 0.1 to 10 weight percent, 0.1 to 5 weight percent, 0.1 to 2 weight percent, 0.2 to 2 weight percent, 0.2 to 1.5 weight percent, 0.2 to 1 weight percent, 0.2 to 0.8 weight percent, 0.2 to 0.6 weight percent, 0.3 to 0.6 weight percent, or 0.4 to 0.6 weight percent.

In embodiments, the corrosion inhibitor formulation includes a coupling agent. The coupling agent may act to mitigate phase separation of components in the corrosion inhibitor formulation. The risk of phase separation may be especially acute in environments with a large temperature range. According to one or more embodiments, the coupling agent is an alkyl imino dipropionic acid sodium salt. In embodiments, the coupling agent is present in the corrosion inhibitor formulation at a concentration of from 0.1 to 10 weight percent, 0.1 to 5 weight percent, to 5 weight percent, 0.3 to 5 weight percent, 0.3 to 3 weight percent, 0.3 to 2 weight percent, to 2 weight percent, 0.5 to 1.5 weight percent, 0.7 to 1.5 weight percent, or 0.8 to 1.2 weight percent.

In some embodiments, the corrosion inhibitor formulation includes an ethoxylated amine. The ethoxylated amine may facilitate film formation and neutralize acids present in the environment. In embodiments, the ethoxylated amine is present in the corrosion inhibitor formulation at a concentration of from 0.1 to 10 weight percent, 0.1 to 5 weight percent, 0.2 to 5 weight percent, 0.3 to 5 weight percent, 0.3 to 3 weight percent, 0.3 to 2 weight percent, 0.5 to 2 weight percent, 0.5 to 1.5 weight percent, 0.7 to 1.5 weight percent, or 0.8 to 1.2 weight percent.

According to one or more embodiments, the corrosion inhibitor formulation includes a supporting component. The supporting component may act cooperatively, along with the active component, to mitigate corrosion. In some embodiments, the supporting component mitigates sweet corrosion in wet environments containing both $CO_2$ and $H_2S$. According to one or more embodiments, the supporting component comprises imidazoline. In embodiments, imidazoline is present in the corrosion inhibitor formulation at a concentration of from 0.1 to 20 weight percent, to 20 weight percent, 0.3 to 20 weight percent, 0.5 to 20 weight percent, 1 to 20 weight percent, 1 to 15 weight percent, 1 to 10 weight percent, 2 to 10 weight percent, 2 to 8 weight percent, or 2 to 6 weight percent.

In embodiments, a process for inhibiting corrosion includes contacting a metallic surface with a corrosion inhibitor formulation according to embodiments described herein. According to embodiments, the metallic surface comprises steel. In some embodiments, the metallic surface comprises carbon steel. In embodiments, the metallic surface may be contacted with a solution containing the corrosion inhibitor formulation at a concentration by weight of 0.5 parts per million to 500 parts per million, 0.5 parts per million to 200 parts per million, 0.5 parts per million to 100 parts per million, 0.5 parts per million to 50 parts per million, 1 part per million to 50 parts per million, 1 part per million to 40 parts per million, 2 part per million to 40 parts per million, 2 part per million to 30 parts per million, 3 part per million to 30 parts per million, 3 part per million to parts per million, 5 part per million to 20 parts per million, or 5 part per million to 15 parts per million. In embodiments, the metallic surface may be contacted with the corrosion inhibitor formulation at least one time, at least two times, at least three times, at least four times, or even at least five times. It should be understood that when the metallic surface is contacted with the corrosion inhibitor formulation multiple times, each contacting may be accomplished using the same or different concentrations of the compound described herein.

Many oil and gas processing facilities such as gas oil separation plants and pipelines include metallic surfaces exposed to sour well fluids. Thus, adding the corrosion inhibitor formulation described herein to the sour well fluids may mitigate corrosion of the metallic surfaces. Thus, according to one or more embodiments, a process for inhibiting corrosion includes adding the corrosion inhibitor formulation described herein to a well fluid to effect a concentration by weight of the formulation in the well fluid of from 0.5 parts per million to 500 parts per million, parts per million to 200 parts per million, 0.5 parts per million to 100 parts per million, 0.5 parts per million to 50 parts per million, 1 part per million to 50 parts per million, 1 part per million to 40 parts per million, 2 part per million to 40 parts per million, 2 part per million to 30 parts per million, 3 part per million to 30 parts per million, 3 part per million to 20 parts per million, 5 part per million to 20 parts per million, or 5 part per million to 15 parts per million.

Corrosion inhibitor formulations described herein may exhibit a higher corrosion inhibition efficiency than conventional corrosion inhibitor formulations. In embodiments, corrosion inhibitor formulations described herein may exhibit a corrosion inhibition efficiency that is at least 5%, at least 10%, at least 15%, at least 20%, at least 25%, or at least 30% greater than conventional corrosion inhibitor formulations. Because embodiments of the corrosion inhibitor formulations described herein exhibit a greater corrosion inhibition efficiency than conventional corrosion inhibitor formulations, a lower dosage of the corrosion inhibitor formulations described herein may provide a metallic surface with the same or even greater protection from corrosion than a higher dosage of a conventional corrosion inhibitor formulation. As such, corrosion inhibitor formulations described herein may be more efficient and cost-effective than conventional corrosion inhibitor formulations.

According to an aspect, either alone or in combination with any other aspect, a compound for inhibiting corrosion includes Formula (I):

(I)

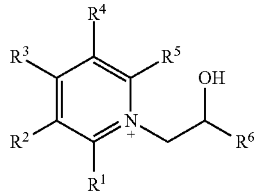

or a salt thereof. $R^1$, $R^2$, $R^3$, $R^4$, and $R^5$ are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide.

According to a second aspect, either alone or in combination with any other aspect, the compound includes Formula (I) where $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl.

According to a third aspect, either alone or in combination with any other aspect, the compound includes Formula (I) where $R^6$ is a substituted or unsubstituted $C_1$ to $C_{24}$ alkyl.

According to a fourth aspect, either alone or in combination with any other aspect, the compound includes Formula (I) where $R^6$ is a substituted or unsubstituted $C_5$ to $C_{15}$ alkyl.

According to a fifth aspect, either alone or in combination with any other aspect, the compound includes Formula (I) where: $R^1$, $R^2$, $R^3$, $R^4$, and $R^5$ are independently hydrogen; and $R^6$ is an unsubstituted $C_5$ to $C_{15}$ alkyl.

According to a sixth aspect, either alone or in combination with any other aspect, a method of making the compound includes reacting a pyridine comprising Formula (II):

(II)

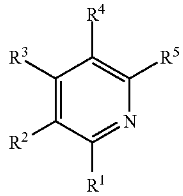

or a salt thereof, with an epoxide comprising Formula (III):

(III)

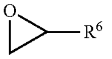

in the presence of an acid to produce the compound. $R^1$, $R^2$, $R^3$, $R^4$, and $R^5$ are independently hydrogen, substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide. $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, substituted or unsubstituted alkynyl, sulfonate, aryl sulfonate, $C_1$ to $C_{24}$ alkyl sulfonate, taurine, carboxylate, amine, alkylamine, arylamine, alkylammonium, arylammonium, sulfonamide, halogen, hydroxy, amide, nitro, cyano, azide, O-alkyl, S-alkyl, silyl, trialkylsilyl, O-silyl, haloalkyl, alkylsulfhydryl, trifluoromethyl, hydrazide, substituted or unsubstituted aryl, heteroaryl, or heterocyclic alkynyl, carboxyalkyl, aminoalkyl, haloalkyl, azidoalkyl, amide, amino acid, or peptide.

According to a seventh aspect, either alone or in combination with any other aspect, the method includes Formula (III) where $R^6$ is a substituted or unsubstituted $C_1$ to $C_{24}$ alkyl, substituted or unsubstituted alkylaryl, substituted or unsubstituted aryl, substituted or unsubstituted heteroaryl, substituted or unsubstituted alkenyl, or a substituted or unsubstituted alkynyl.

According to an eighth aspect, either alone or in combination with any other aspect, the method includes Formula (III) where $R^6$ is a substituted or unsubstituted $C_1$ to $C_{24}$ alkyl.

According to a ninth aspect, either alone or in combination with any other aspect, the method includes Formula (III) where $R^6$ is a substituted or unsubstituted $C_5$ to $C_{15}$ alkyl.

According to a tenth aspect, either alone or in combination with any other aspect, the method includes Formula (II) where $R^1$, $R^2$, $R^3$, $R^4$, and $R^5$ are independently hydrogen; and Formula (III) where $R^6$ is an unsubstituted $C_5$ to $C_{15}$ alkyl.

According to an eleventh aspect, either alone or in combination with any other aspect, a sour well fluid includes the compound at a concentration by weight of 0.1 parts per million to 100 parts per million of the well fluid.

According to a twelfth aspect, either alone or in combination with the eleventh aspect, the sour well fluid includes the compound at a concentration by weight of 0.2 parts per million to 20 parts per million.

According to a thirteenth aspect, either alone or in combination with any other aspect, the sour well fluid includes petroleum hydrocarbons.

According to a fourteenth aspect, either alone or in combination with any other aspect, a formulation for inhibiting corrosion includes the compound and water.

According to a fifteenth aspect, either alone or in combination any other aspect, the formulation includes a synergist.

According to a sixteenth aspect, either alone or in combination with any other aspect, the formulation includes a nonionic surfactant, imidazoline, a secondary solvent, a coupling agent, and an ethoxylated amine.

According to a seventeenth aspect, either alone or in combination with any other aspect, the formulation includes the compound at a concentration of from 5 to 25 weight percent; water at a concentration of from 40 to 90 weight percent; imidazoline at a concentration of from 1 to 10 weight percent; and the synergist includes thioglycollic acid, 2-mercaptoethanol, or a mixture thereof.

According to an eighteenth aspect, either alone or in combination with any other aspect, a process for inhibiting corrosion includes contacting a metallic surface with the formulation.

According to a nineteenth aspect, either alone or in combination with the eighteenth aspect, the metallic surface includes steel.

According to a twentieth aspect, either alone or in combination with any other aspect, a process for inhibiting corrosion includes adding the formulation to a well fluid to effect a concentration by weight of the formulation in the well fluid of from 0.5 parts per million to 500 parts per million.

EXAMPLES

Using embodiments described above, an exemplary corrosion inhibitor was prepared and used according to the following examples. The examples are illustrative in nature, and should not be understood to limit the subject matter of the present disclosure.

Example 1: Preparation of Active Component 1

Preparation of Active Component 1 is achieved substantially as depicted in Scheme I:

Scheme I

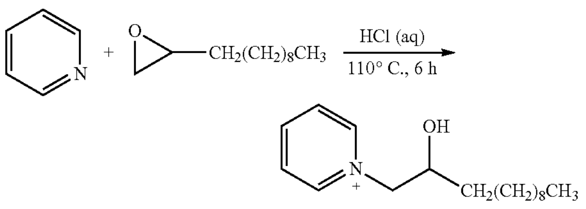

Active Component 1

Briefly, pyridine (1.5 moles, Aldrich) and hydrochloric acid (1 mole, 37% solution in water, Aldrich) were added to a round bottom flask. The resulting mixture was purged with nitrogen and stirred at room temperature for 10 minutes. 1,2-epoxydodecane (1 mole, Aldrich) was added and the resulting mixture was stirred for 30 minutes at room temperature. The reaction mixture was then stirred at 110° C. for 6 hours before being cooled to room temperature. Excess pyridine was removed by rotary evaporation. Active Component 1 was then precipitated by addition of diethyl ether (Aldrich).

The structure of Active Component 1 was confirmed by nuclear magnetic resonance (NMR) spectroscopy. Specifically, a sample of Active Component 1 was dissolved in deuterated water ($D_2O$) and its $^1H$ NMR and $^{13}C$ NMR spectra were obtained using a 500 MHz NMR spectrometer with appropriate acquisition parameters. Chemical shifts were set to those of deuterated trimethylsilylpropanoic acid (0 ppm). The $^1H$ NMR and $^{13}C$ NMR spectra are shown in FIG. 1A and FIG. 1B respectively.

Referring to FIG. 1A, the $^1H$ NMR spectrum of Active Component 1 shows the pyridinium protons having a chemical shift of 9.01 ppm, 8.78 ppm, and 8.27 ppm. The protons on the carbon alpha to the pyridinium have a chemical shift of 5.00 ppm and 4.63 ppm. The proton on the carbon beta to the pyridinium and alpha to the hydroxy group has a chemical shift of 4.25 ppm. The protons on the carbon gamma to the pyridinium and beta to the hydroxy group have a chemical shift of 1.72 ppm. The remainder of the $CH_2$ protons are at 1.48 ppm while the $CH_3$ protons are present at 1.06 ppm.

Figure 1B:
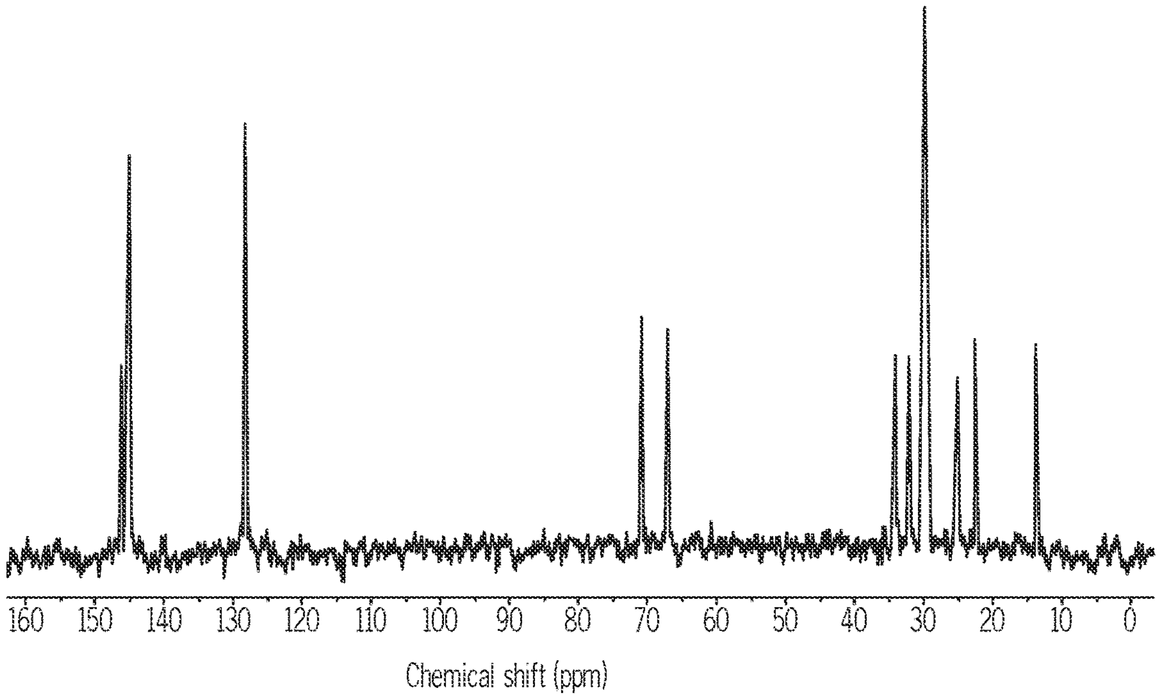
FIG. 1B is a $^{13}C$ NMR spectrum of an embodiment of an active component according to embodiments described herein.

Referring to FIG. 1B, the $^{13}C$ NMR spectrum of Active Component 1 shows the pyridinium carbons having a chemical shift of 146.3 ppm, 145.0 ppm, and 128.3 ppm. The carbon alpha to the pyridinium has a chemical shift of 66.9 ppm. The carbon beta to the pyridinium and alpha to the hydroxy group has a chemical shift of 70.5 ppm. The remainder of the carbons have chemical shifts between 10.0 ppm and 35.0 ppm.

Example 2: Preparation of Corrosion Inhibitors

Corrosion Inhibitor Formulation 1 (CIF-1), Comparative Corrosion Inhibitor Formulation 1 (CCIF-1), and Comparative Corrosion Inhibitor Formulation 2 (CCIF-2) were prepared according to the general formula shown in Table 1. The identity of the Active Compound in each corrosion inhibitor formulation is shown in Table 2.

TABLE 1

General Formula of Corrosion Inhibitor Formulations

| Component | Weight (%) |
|---|---|
| Water | 70.4 |
| Thioglycollic Acid | 2.8 |
| 2-Merceptoethanol | 1.5 |
| Ethylene Glycol | 1.5 |
| Ethylene Diamine | 1.5 |
| Long Chain Ethoxylated Alcohol | 0.5 |
| Ethoxylated Amine | 0.9 |
| Alkyl Imino Dipropionic Acid Sodium Salt | 0.9 |
| Imidazoline | 5.0 |
| Active Component | 15.0 |

TABLE 2

Identity of the Active Component in Each Corrosion Inhibitor Formulation

| Corrosion Inhibitor | Active Component |
|---|---|
| CIF-1 | Active Component 1 |
| CCIF-1 | Dodecyl pyridinium |
| CCIF-2 | Imidazoline |

Example 3: Performance of Corrosion Inhibitors

The corrosion inhibition efficiency of CIF-1, CCIF-1, CCIF-2, and a conventional corrosion inhibitor formulation (CCIF-3) were evaluated in four experiments. In CCIF-3, the active component was an alkyl pyridinium benzyl chloride, and the inactive components included an alkoxylated fatty amine, nonylphenol, and an alcohol. Experiments were performed using a four-liter high temperature and high pressure (HTHP) autoclave rotating cage made from C-276 alloy, which withstands harsh corrosive environments. Briefly, carbon steel C-1018 coupons were cleaned and degreased following ASTM G 1. The coupons were positioned in a fixed cage made from polyether ether ketone (PEEK), which was then mounted in the autoclave. To simulate field conditions, a 1:1 mixture of kerosene and water comprising the corrosion inhibitor formulation was mixed at room temperature. The water used had a pH of 6.6. The geochemical analysis of the water is shown in Table 3. The concentration of the corrosion inhibitor formulation in the mixture for each respective test is shown in Table 4. After 2 hours, the kerosene was removed and the remaining water was used in the autoclave for the test. The autoclave was pressurized to 250 psi with a gas comprising 7 mole % $CO_2$, 3 mole % $H_2S$, and 90 mole % $N_2$ and heated to a temperature of 182° F. The cage was rotated at 400 RPM for 24 hours.

TABLE 3

Water Geochemical Analysis

| Analyte | Concentration (mg/L) |
|---|---|
| Na | 29,500 |
| Ca | 8,210 |
| Mg | 1,080 |
| Cl | 61,800 |
| $SO_4$ | 1,300 |
| $HCO_3$ | 662 |
| Total Dissolved Solids | 102,552 |

The corrosion rate (CR) in mils per year was calculated for each corrosion inhibitor formulation using equation (1):

$$CR = \frac{\Delta W \times 22{,}300}{D \times A \times T} \times 100\%, \tag{1}$$

where ΔW is the weight loss of coupon in milligrams, D is the density of the carbon steel coupons (7.89 g/cm$^3$), A is the area of the exposed coupon (7.86 square inches) and T is the exposure time (24 hours). The corrosion rate of each corrosion inhibitor formulation is provided in Table 4.

The corrosion inhibition efficiency (IE %) of each corrosion inhibitor formulation was calculated using equation (2):

$$IE\ \% = \frac{(CR_{blank} - CR_{inhib})}{CR_{blank}} \times 100\%, \tag{2}$$

where $CR_{blank}$ is the corrosion rate without inhibitor and $CR_{inhib}$ is the corrosion rate with the inhibitor. The corrosion inhibition efficiency of each corrosion inhibitor formulation is provided in Table 4.

TABLE 4

Corrosion Inhibition Efficiency of Corrosion Inhibitor Formulations

| Corrosion Inhibitor | Concentration (ppm) | Corrosion Rate (mils per year) | Corrosion Inhibition Efficiency (%) |
|---|---|---|---|
| CIF-1 | 10 | 4.8 | 70.5 |
| CCIF-1 | 20 | 8.1 | 49.5 |
| CCIF-2 | 100 | 9.9 | 38.0 |
| CCIF-3 | 10 | 9.6 | 40.3 |

The corrosion inhibition results shown in Table 4 indicate that CIF-1, which includes Active Component 1, exhibited significantly superior corrosion inhibition efficiency to all the comparative corrosion inhibitor formulations. In particular, CIF-1 exhibited superior performance to CCIF-3, which is a conventional corrosion inhibitor formulation used to inhibit corrosion in gas oil separation plants in a wet sour environment in the oil and gas industry. Further, CIF-1 exhibited superior corrosion inhibition efficiency to CCIF-1, even at half the concentration. CIF-1 and CCIF-1 are identical other than the presence of the hydroxyl group on the alkyl chain of the active component. Thus, a comparison of CIF-1 and CCIF-1 reveals that the presence of the hydroxyl group on the active component plays a crucial role in achieving the improved corrosion inhibition efficiency of CIF-1.

The corrosion inhibition results shown in Table 4 also reveal that imidazoline is not responsible for the majority of the corrosion inhibition efficiency exhibited in corrosion inhibitor formulations according to embodiments described herein. In particular, comparing CIF-1, which contains 15 weight % Active Component 1 and 5 weight % imidazoline, with CCIF-2, which contains 20 weight % imidazoline, reveals that CIF-1 is superior to CCIF-2 in corrosion inhibition efficiency even at one tenth the concentration. Comparing the corrosion inhibition efficiency of CCIF-1 with CCIF-2 also reveals that an active component comprising a pyridinium on an alkyl chain absent a hydroxyl group provides superior corrosion inhibition performance to imidazoline, even at one fifth the concentration. Thus, it is believed that the presence of both the pyridinium and the hydroxyl group on Active Component 1 is responsible for the improved corrosion inhibition exhibited by CIF-1 compared with CCIF-1, CCIF-2, and CCIF-3.

It should be understood that any ranges provided herein include the endpoints unless stated otherwise.

It should be understood that any two quantitative values assigned to a property may constitute a range of that property, and all combinations of ranges formed from all stated quantitative values of a given property are contemplated in this disclosure.

The subject matter of the present disclosure has been described in detail and by reference to specific embodiments. It should be understood that any detailed description of a component or feature of an embodiment does not necessarily imply that the component or feature is essential to the particular embodiment or to any other embodiment. Further, it should be apparent to those skilled in the art that various modifications and variations can be made to the described embodiments without departing from the spirit and scope of the claimed subject matter.

What is claimed is:

1. A formulation comprising: a compound for inhibiting corrosion; a synergist; a nonionic surfactant; an imidazoline; a secondary solvent; a coupling agent; an ethoxylated amine; and water, the compound comprising:

Formula (I)

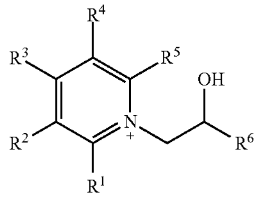

(I)

or a salt thereof, where:

$R^1$, $R^2$, $R^3$, $R^4$, and $R^5$ are independently hydrogen; and $R^6$ is an substituted $C_5$ to $C_{15}$ alkyl; and wherein the synergist comprises thioglycollic acid, 2-mercaptoethanol, or a mixture thereof; and wherein the formulation comprises:

from 5 to 25 weight percent of the compound;

from 1 to 10 weight percent imidazoline;

from 40 to 90 weight percent water; and 0.1 parts per million to 100 parts per million of the compound.

2. The formulation of claim 1, where the compound is present at a concentration, by weight, of 0.2 parts per million to 20 parts per million.

3. The formulation of claim 1 further comprising petroleum hydrocarbons.

4. A process for inhibiting corrosion comprising contacting a metallic surface with the formulation of claim 1.

5. The process of claim 4, where the metallic surface comprises steel.

6. A process for inhibiting corrosion comprising adding the formulation of claim 1 to a well fluid to effect a concentration, by weight, of the formulation in the well fluid of from 0.5 parts per million to 500 parts per million.

* * * * *